United States Patent [19]

Fehr et al.

[11] 4,348,392
[45] Sep. 7, 1982

[54] 8α-SUBSTITUTED ERGOLINE-I DERIVATIVES

[75] Inventors: Theodor Fehr, Dornach; Paul Stadler, Biel-Benken; Peter Stütz, Bottmingen, all of Switzerland

[73] Assignee: Sandoz Ltd., Basel, Switzerland

[21] Appl. No.: 189,295

[22] Filed: Sep. 22, 1980

Related U.S. Application Data

[63] Continuation of Ser. No. 912,876, Jun. 5, 1978, abandoned, which is a continuation of Ser. No. 825,598, Aug. 19, 1977, abandoned, which is a continuation of Ser. No. 725,431, Sep. 22, 1976, abandoned, which is a continuation-in-part of Ser. No. 595,161, Jul. 11, 1975, abandoned.

[30] Foreign Application Priority Data

Jul. 19, 1974 [CH] Switzerland .................. 9983/74
Aug. 13, 1974 [CH] Switzerland .................. 11031/74
Jan. 2, 1976 [GB] United Kingdom .................. 48/76

[51] Int. Cl.³ .................. C07D 457/12; A61K 31/48
[52] U.S. Cl. .................. 424/246; 424/248.4; 424/250; 424/261; 544/60; 544/125; 544/361; 546/67; 546/68
[58] Field of Search .................. 546/67, 68; 424/261, 424/250, 248.4, 246; 544/60, 125, 361

[56] References Cited

U.S. PATENT DOCUMENTS

| | | | |
|---|---|---|---|
| 2,533,698 | 12/1950 | Stoll et al. | 546/68 |
| 3,185,695 | 5/1965 | Bernardi et al. | 546/68 |
| 3,218,323 | 11/1965 | Hofmann et al. | 546/68 |
| 3,232,943 | 2/1966 | Hofmann et al. | 546/68 |
| 3,245,996 | 4/1966 | Hofmann et al. | 546/67 |
| 3,270,020 | 8/1966 | Hofmann et al. | 546/68 |
| 3,557,118 | 1/1971 | Arcamone et al. | 546/67 |
| 3,732,231 | 5/1973 | Semonsky et al. | 546/67 |
| 3,880,856 | 4/1975 | Bach et al. | 546/67 |
| 3,904,757 | 9/1975 | Slater | 424/261 |
| 3,920,664 | 11/1975 | Clemens et al. | 424/261 |
| 3,922,347 | 11/1975 | Bach et al. | 424/261 |

FOREIGN PATENT DOCUMENTS 831488 1/1976 Belgium .................. 546/67
1041862 9/1966 United Kingdom.

OTHER PUBLICATIONS

Clemens et al.; Endocrinology; vol. 94; p. 1171 (1974).

*Primary Examiner*—Mary C. Lee
*Attorney, Agent, or Firm*—Gerald D. Sharkin; Robert S. Honor; Thomas O. McGovern

[57] ABSTRACT

This invention provides new compounds of formula I,

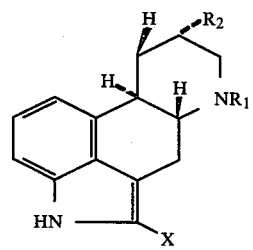

wherein
  X is hydrogen, chlorine or bromine,
  $R_1$ is methyl or ethyl, and
  $R_2$ is $CH_2$—CN, or a group $NR_3R_4$, wherein
    $R_3$ is hydrogen or alkyl of 1 to 4 carbon atoms, and
    $R_4$ is $SO_2R_5$, wherein $R_5$ is alkyl of 1 to 4 carbon atoms, mono- to tri-halogenalkyl of 1 to 4 carbon atoms, phenyl, pyridyl, phenyl monosubstituted by halogen or alkoxy of 1 to 4 carbon atoms, or a group $NR_6R_7$, wherein each of
      $R_6$ and $R_7$ is independently hydrogen or alkyl of 1 to 4 carbon atoms, or
      $R_6$ and $R_7$ together are one of the groups $(CH_2)_n$ or $(CH_2)_2$—A—$(CH_2)_2$, wherein
        n is a number from 3 to 7, and
        A is oxygen, sulphur or nitrogen substituted by alkyl of 1 to 4 carbon atoms or phenyl, useful as prolactin secretion agents and antiparkinson agents.

29 Claims, No Drawings

8α-SUBSTITUTED ERGOLINE-I DERIVATIVES

This is a continuation of application Ser. No. 912,876, filed June 5, 1978 now abandoned, which in turn is a continuation of application Ser. No. 825,598, filed Aug. 19, 1977, now abandoned, which in turn is a continuation of application Ser. No. 725,431, filed Sept. 22, 1976, now abandoned, which in turn is a continuation-in-part of Ser. No. 595,161, filed July 11, 1975, now abandoned.

The present invention relates to new organic compounds.

In accordance with the invention there are provided new compounds of formula I,

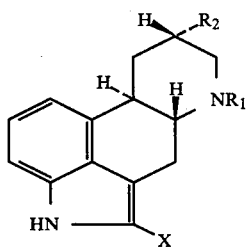

wherein
X is hydrogen, chlorine or bromine,
$R_1$ is methyl or ethyl, and
$R_2$ is $CH_2$—CN, or a group $NR_3R_4$, wherein
   $R_3$ is hydrogen or alkyl of 1 to 4 carbon atoms, and
   $R_4$ is formyl, alkanoyl of 2 to 5 carbon atoms in the aggregate thereof, alkoxycarbonyl of 2 to 5 carbon atoms in the aggregate thereof, mono- to trihalogenalkoxycarbonyl of 3 to 5 carbon atoms in the aggregate thereof, the alkoxy radical of which is substituted by halogen in a position other than α to the oxygen, or the radical $SO_2R_5$, wherein $R_5$ is alkyl of 1 to 4 carbon atoms, mono- to tri-halogenalkyl of 1 to 4 carbon atoms, phenyl, pyridyl, phenyl monosubstituted by halogen or alkoxy of 1 to 4 carbon atoms, or a group $NR_6R_7$, wherein each of
      $R_6$ and $R_7$ is independently hydrogen or alkyl of 1 to 4 carbon atoms, or
      $R_6$ and $R_7$ together are one of the groups $(CH_2)_n$ or $(CH_2)_2$-A-$(CH_2)_2$, wherein
         n is a number from 3 to 7, and
         A is oxygen, sulphur or nitrogen substituted by alkyl of 1 to 4 carbon atoms or phenyl.

X preferably signifies chlorine, especially hydrogen.
$R_1$ especially denotes methyl.
$R_3$ especially signifies hydrogen, methyl or ethyl, preferably hydrogen.

When the radical $R_4$ or $R_5$ has a halogen substituent, this signifies fluorine, chlorine or bromine. When the radical $R_4$ or $R_5$ is di- or trihalogenated, the halogen substituents of these radicals are preferably identical.

The preferred radicals $R_4$ are methoxycarbonyl, ethoxycarbonyl, (2,2,2-tri-halogenalkoxy)carbonyl or the group $SO_2R_5$ preferably wherein $R_5$ is alkyl or phenyl.

Any halogen substituents in the radical $R_4$ especially signify fluorine or chlorine.

When $R_5$ is alkyl of 1 to 4 carbon atoms or mono- to tri-halogenalkyl of 1 to 4 carbon atoms, these radicals preferably contain 1 or 2 carbon atom.

When $R_5$ is phenyl monosubstituted by alkoxy of 1 to 4 carbon atoms, the alkoxy substituent especially contains 1 or 2, preferably 1 carbon atom.

$R_5$ preferably signifies methyl, phenyl, pyridyl or a group $NR_6R_7$.

When both of $R_6$ and $R_7$ are alkyl of 1 to 4 carbon atoms, each of these groups preferably contains 1 or 2 carbon atoms.

n is preferably 5.

A especially signifies oxygen, or nitrogen substituted by methyl or phenyl.

$NR_6R_7$ preferably signifies amino, dimethylamino, diethylamino or the 4-methyl-1-piperazinyl group.

Further, in accordance with the invention a compound of formula I may be obtained by a process comprising (a) producing a compound of formula Ia,

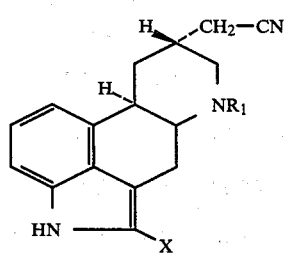

wherein X and $R_1$ are as defined above,
by exchanging the radical Z for a cyano group in a compound of formula II,

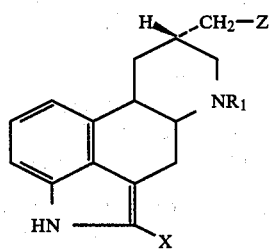

wherein
Z is a radical capable of being exchanged in a nucleophilic substitution reaction, and
X and $R_1$ are as defined above, or (b) producing a compound of formula Ib,

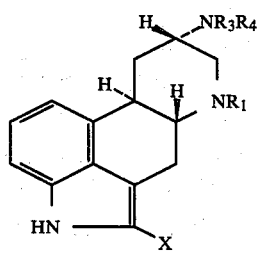

wherein X, $R_1$, $R_3$ and $R_4$ are as defined above, by acylating a compound of formula III,

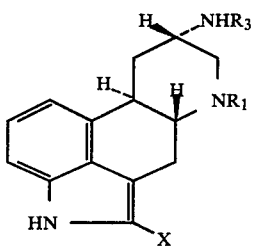

wherein X, $R_1$ and $R_3$ are as defined above, with a reactive functional derivative of an acid $R_4OH$, wherein $R_4$ is as defined above.

The reaction of a compound of formula II for the obtention of a compound of formula Ia [process (a)] and the reaction of a compound of formula III to obtain a compound of formula Ib [process (b)] may be effected in accordance with known methods.

The radical Z in the compounds of formula II may, for example, signify halogen such as chlorine or bromine, or an aliphatic or aromatic sulphonyloxy radical, preferably the mesyloxy or the p-tosyloxy radical. The reaction may, for example, be effected by reacting a compound of formula II with a cyano group donor, e.g. an alkali metal cyanide such as sodium or potassium cyanide.

The reaction is preferably effected in solution. It is convenient to use aprotic solvents such as dimethyl formamide, hexamethylphosphoric acid triamide or acetonitrile, if necessary in admixture with a small portion of water.

The reaction is preferably effected with heating, e.g. to 50°–100° C.

Process (b) is an N-acylation process. The following reactive functional derivatives of $R_4OH$ may, for example, be used for the introduction of the radical $R_4$ in a compound of formula III: for the introduction of the formyl radical the mixed anhydride of formic acid with acetic acid, for the introduction of the remaining radicals $R_4$ a halide corresponding to the acid, e.g. the acid chloride or acid bromide, and for the introduction of an alkanoyl radical the corresponding anhydrides [(alkanoyl)$_2$O].

Process (b) is conveniently effected in solution. Suitable solvents are, for example, methylene chloride and dioxane. When an anhydride is used as acylating agent it is also possible to use an excess of anhydride as solvent.

The reaction is generally conveniently effected at a reaction temperature between −10° C. and about room temperature. However, the N-formylation with the mixed anhydride of acetic acid and formic acid is conveniently effected at a slightly elevated temperature, e.g. about 40°–60° C.

Process (b) is conveniently effected in the presence of a tertiary base such as triethylamine, or preferably in the presence of pyridine or a homologue thereof.

The compounds obtained in accordance with processes (a) and (b) may be obtained in the form of a base or in the form of acid addition salts thereof. Acid addition salt forms may be produced from the free bases in known manner and vice versa.

The starting materials are known or may be produced in accordance with known methods, e.g. as described in the examples.

In the following non-limitative examples all temperatures are indicated in degrees Centigrade. The compounds of formula I are herein named 8α-ergoline I compounds. The 8α-cyanomethylergoline I compounds of formula Ia may also be named (5R,8R,10S)-8-cyanomethylergoline I compounds, and the 8α-aminoergoline I compounds of formula Ib may be named (5R,8S,10S)-8-aminoergoline I compounds.

EXAMPLE 1

6-methyl-8α-cyano-methyl ergoline I 3.35 g (10 millimols) of 6-methyl-8α-mesyloxymethyl ergoline I are dissolved in 20 cc of dimethyl formamide, and a solution of 3.25 g of potassium cyanide (50 millimols) in 4 cc of water is added. After standing at 80° for 48 hours, the reaction solution is poured into an excess of a 2 normal soda solution, the precipitate is filtered off, dried in the air and subsequently chromatographed on 150 g of aluminium oxide activity II-III. The title compound is eluted with 0.2% of methanol in methylene chloride and crystallizes from methanol (M.P. 160° to 162°, $[\alpha]_D^{20} = -96°$ (c=0.3, dimethyl formamide).

The 6-methyl-8α-mesyloxymethyl ergoline I, required as starting material, is obtained as follows:

(a) 100 g of Δ7,8-lysergic acid methyl ester are dissolved in 900 cc of dimethyl formamide while heating, dilution is effected with 1.5 liters of glacial acetic acid, and after the addition of 10 g of platinum oxide, hydrogenation is effected at +40°–50° and normal pressure until the take up of hydrogen stops. The catalyst is filtered off and the filtrate is further hydrogenated under the above conditions after the addition of 5 g of platinum oxide. Working up is effected by filtering and evaporating the filtrate to dryness. The resulting resin is dissolved in 1.5 liters of methylene chloride containing 5% of methyl alcohol, the solution is stirred well with 20 g of active charcoal, filtration is effected, after cooling well, it is slowly covered with a layer of one liter a 2 N sodium carbonate solution and carefully shaken. The aqueous phase is again extracted twice with 500 cc of methylene chloride. After drying the organic phase over sodium sulphate and concentrating to about 1/5 of the original volume, dilution with about 500 cc of ether and scratching are effected. After standing at 0° for 2 hours, 9,10-dihydro-isolysergic acid methyl ester I crystallizes. Working up of the evaporation residue in accordance with known methods yields an additional amount of 9,10-dihydro-isolysergic acid methyl ester I. After recrystallization from methylene chloride/ethyl acetate or ethanol, the ester has a M.P. of 178° to 180°, $[\alpha]_D^{20} = -82°$ (c=1, pyridine).

(b) 38 g of lithium aluminium hydride are suspended in 2.5 liters of absolute tetrahydrofuran under nitrogen, cooling is effected to 0°, and a solution of 200 g of 9,10-dihydro-isolysergic acid methyl ester I in 2.5 liters of absolute tetrahydrofuran is added dropwise within 15 minutes while stirring vigorously. The reaction product is subsequently diluted with 2.5 liters of absolute tetrahydrofuran and stirred for a further 30 minutes. Working up is effected by the careful successive dropwise addition of 100 cc of ethyl acetate, 100 cc of methanol and 50 cc of water. Dilution is subsequently effected with 2 liters of 30% methanol in methylene chloride and filtration is effected. The residue is again boiled out 4 times with 1 liter amounts of 30% methanol in methylene chloride. After concentration and crystallization from methanol, the combined filtrates yield 9,10-dihydro-isolysergol I having a M.P. of 189° to 193°. A further amount of 9,10-dihydro-isolysergol I may be isolated from the mother liquor by chromatography.

(c) 100 g of 9,10-dihydro-lysergol I are suspended in 500 cc of absolute pyridine and 1.1 liters of absolute acetonitrile, and a solution of 80 cc of methane-sulphochloride in 200 cc of absolute acetonitrile is added dropwise at 0° while stirring. After removing the cooling bath, the reaction mixture is stirred for a further hour at room temperature, whereby a yellowish precipitate results. Working up is effected by again cooling to 0° and adding a 2 N ammonia solution until an alkaline reaction is obtained. After scratching, 6-methyl-8α-methane-sulphonyloxymethyl ergoline I crystallizes (M.P. 139°-141°; $[\alpha]_D^{20} = -54.6°$ (c=1, dimethyl formamide).

The following compounds of formula Ia are obtained in a manner analogous to that described in process (a) above, by using the corresponding compounds of formula II (Z=mesyloxy):

| Ex. Nr. | X  | $R_1$    | M.P.                              |
|---------|----|----------|-----------------------------------|
| 2       | Cl | $CH_3$   | of the hydrochloride 267-268°     |
| 3       | H  | $C_2H_5$ | 182° (base)                       |

EXAMPLE 4

6-methyl-8α-N,N-dimethyl-sulphamylamino ergoline I 2.41 g (10 millimols) of 6-methyl-8α-amino ergoline I are dissolved in a mixture of 200 cc of methylene chloride and 25 cc of absolute pyridine, and a solution of 3.58 g (25 millimols) of dimethylsulphamyl chloride in 25 cc of methylene chloride is added dropwise with stirring at room temperature. After stirring for 12 hours, working up is effected as described in Example 1. The orange red crude base is chromatographed on a 50-fold quantity of silica gel, whereby the title compound is eluted with 2% of methanol in methylene chloride. M.P. 223°-226° from ethanol; yellowish needles. $[\alpha]_D^{20} = -51.6°$ (c=0.5 in pyridine).

The following compounds of formula Ib are obtained in a manner analogous to that described in Example 4, by acylating the corresponding compounds of formula III with the acid chloride:

| Ex. Nr. | X | $R_1$  | $R_3$ | $R_4$           | M.P. |
|---------|---|--------|-------|-----------------|------|
| 5       | H | $CH_3$ | H     | $CO_2C_2H_5$    | from 120° (dec.) (base) $[\alpha]_D^{20} = -29°$ (c = 0,35; dimethyl formamide) |
| 6       | H | $CH_3$ | H     | $CO_2CH_3$      | of the hydrochloride: 279-280° |
| 7       | H | $CH_3$ | H     | $COC(CH_3)_3$   | of the base: 199-200° |
| 8       | H | $CH_3$ | H     | $CO_2CH_2CCl_3$ | 117-119° |
| 9       | H | $CH_3$ | H     | $SO_2NH_2$      |      |
| 10      | H | $CH_3$ | H     | $SO_2NH-C(CH_3)_3$ |   |
| 11      | H | $CH_3$ | H     | $SO_2-N\langle\rangle$ (hexyl ring) |  |
| 12      | H | $CH_3$ | H     | $SO_2-N\langle\rangle NCH_3$ (piperazine with NCH_3) |  |

EXAMPLE 13

6-methyl-8α-formylamino ergoline I 2.41 g (10 millimols) of 6-methyl-8α-amino ergoline I are dissolved in 5 cc of formic acid, and 5 cc of acetic anhydride are added dropwise at 50°-60° while stirring. After stirring for one hour, gas evolution stops; cooling is subsequently effected to 0°, and the reaction mixture is carefully neutralized with 4 N potash solution, and extraction is effected with chloroform containing methanol. After drying and concentrating the organic phases by evaporation, the title compound crystallizes from ethanol, and is obtained in pure form after recrystallization from methylene chloride/ethanol. Non-characteristic M.P. (from 250° decomp.)

$[\alpha]_D^{20} = +23°$ (c=0.3, pyridine).

EXAMPLE 14

6-methyl-8α-pivaloylamino ergoline I

The process is effected in a manner analogous to that described in Example 7, except that pivalic acid anhydride is used in place of pivalic acid chloride as acylating agent, whereby the title compound, having a M.P. of 199° to 200°, is obtained.

Following Example 4 the following compounds of formula I are also produced, wherein X is Br, $R_1$ is $CH_3$ and $C_2H_5$, $R_3$ is n-Bu and $R_4$ is:

COO"Bu
COOCH$_2$CHClCH$_3$
SO$_2$"Bu
SO$_2$CH$_2$Cl"Pr
SO$_2$CHCl$_2$CH$_3$
SO$_2$CH$_2$CCl$_3$
SO$_2$C$_6$H$_5$
SO$_2$—2-Pyridyl

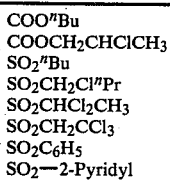

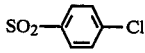

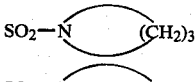

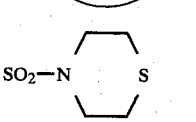

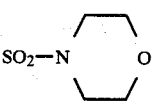

The following compounds of formula I wherein $R_1$ is methyl are also produced in a manner analogous to that described in Example 4, wherein:

| $R_2$ | X | M.Pt. | $[\alpha]_D^{20}$ (c in DMF) |
|---|---|---|---|
| (a) —NHSO$_2$N(C$_2$H$_5$)$_2$ | H | 201–2° C.[1] | −57° (0.3) |
| (b) —NHSO$_2$NH—C(CH$_3$)$_3$ | H | 209–13° C.[2] (decomp.) | +7° (1) |
| (c) —NHSO$_2$-(3-pyridyl) | H | 262–6° C.[1] | −59° (0.5) |
| (d) —NHSO$_2$-phenyl | H | 199–201° C.[1] | −55° (0.5) |
| (e) —NHSO$_2$CF$_3$ | H | 206–8° C.[1] | −45° (0.45) |
| (f) —NHSO$_2$CH$_3$ | H | 219–20° C.[1] (decomp.) | −69° (0.5) |
| (g) —NH—CO—OCH$_2$—CCl$_3$ | H | 216–8° C.[3] (decomp.) | −25° (0.4) |
| (h) —NHSO$_2$N(CH$_3$)$_2$ | Br | 253–6° C.[4] | +7° (0.5) |

[1] as base
[2] as hydrochloride with 1 mole H$_2$O
[3] as hydrogen tartrate
[4] as hydrochloride The compounds of formula I are useful because they possess pharmacological activity in animals. In particular, the compounds of formula I are useful as central dopaminergic stimulant agents, for example, for treating Morbus Parkinson, as indicated by standard tests, for example according to the principles of U. Ungerstedt Acta Physiol.Scand.Suppl. (1971) 367, 69–93, by an induction of contralateral turning in rats lesioned unilaterally in the substantia nigra by 6-hydroxydopamine an i.p. administration of from about 1 to about 40 mg/kg animal body weight and by an induction of dose dependent stereotyped sniffing, licking and biting behaviour in the rat according to the following test:

Rats, 180–222 g, are placed in perspex cylinders of 30 cm diameter on a wire grid floor. After 30 minutes to allow acclimatisation to the cage, the rats are injected with the compound under investigation. The behaviour of the rats is observed for 2 minutes at 30 minute intervals for 2 hours and then at 60 minute intervals for a total of up to 7 hours. The degree of stereotyped behaviour observed is assessed using a scoring system based on that described by Costall, Naylor and Olley [Euro J. Pharmac. 18, 83–94 (1972)].

The scores and criteria are as follows:
1. Intermittent sniffing
2. Persistent sniffing, occasional licking
3. Licking, occasional biting
4. Intense and persistent biting In this test the compounds are administered i.p. at from 1 to 40 mg/kg animal body weight.

For the above mentioned use the dosage will, of course, vary depending on the compound employed, mode of administration and therapy desired. However, in general, satisfactory results are obtained when administered at a daily dosage of from 0.005 mg to about 50 mg per kg animal body weight, conveniently given in divided doses 2 to 4 times a day or in sustained release form. For the larger mammal, the total daily dosage is in the range from about 0.5 to about 100 mg, preferably from 1 to 50 mg, and dosage forms suitable for oral administration comprise from about 0.1 mg to about 50 mg of the compounds admixed with a solid or liquid pharmaceutical carrier or diluent.

The Example 1 compound shows interesting activity.

Additionally the compounds are useful as agents showing prolactin secretion inhibition activity for example for inhibiting lactation and Galactorrhea as indicated in standard tests, for example, in rats by an inhibition of ovum implantation as follows:

The compound under investigation is administered to female rats 5 days after coitus and shown to be sperm positive according to the vaginal smear test. The rats are sacrificed on day 12 and their uteri are examined by means of the Salewski reaction for proof that the nidations process has been interrupted [Arch.exp.Path.Pharm. 247, 367 (1967)].

The compounds are administered s.c. at from about 0.01 to about 3 mg/kg animal body weight.

For the above mentioned use the dosage will, of course, vary depending on the compound employed, mode of administration and therapy desired. However, in general, satisfactory results are obtained when administered at a daily dosage of from 0.001 mg to about 3 mg per kg animal body weight, conveniently given in divided doses 2 to 4 times a day or in sustained release form. For the larger mammal, the total daily dosage is in the range from about 0.05 to about 10 mg, and dosage forms suitable for oral administration comprise from about 0.01 mg to about 5 mg of the compounds admixed with a solid or liquid pharmaceutical carrier or diluent.

The Example 4 compound shows interesting activity.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be formulated in conventional manner, so as to be, for example, a solution or a tablet.

In one group of compounds $R_2$ is CH$_2$.CN. In another group of compounds $R_2$ is —NHR, wherein R is formyl, alkanoyl, alkoxycarbonyl or

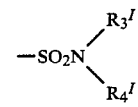

wherein $R_3$ and $R_4$ are alkyl or together are —[CH$_2$]$_n$—, wherein n is from 3 to 5.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the

We claim:
1. A compound of formula I,

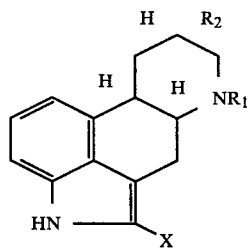

wherein
X is hydrogen, chlorine or bromine,
$R_1$ is methyl or ethyl, and
$R_2$ is a group $NR_3R_4$, wherein
  $R_3$ is hydrogen or alkyl of 1 to 4 carbon atoms, and
  $R_4$ is $SO_2R_5$,
    wherein $R_5$ is alkyl of 1 to 4 carbon atoms, mono- to tri-halogenalkyl of 1 to 4 carbon atoms, phenyl, pyridyl, phenyl monosubstituted by halogen or alkoxy of 1 to 4 carbon atoms, or a group $NR_6R_7$, wherein each of
    $R_6$ and $R_7$ is independently hydrogen or alkyl of 1 to 4 carbon atoms, or
    $R_6$ and $R_7$ together are one of the groups $(CH_2)_n$ or $(CH_2)_2-A-(CH_2)_2$, wherein
    n is a number from 3 to 7, and
    A is oxygen, sulphur or nitrogen substituted by alkyl of 1 to 4 carbon atoms or phenyl,
or a pharmaceutically acceptable acid addition salt.

2. A method of treating Morbus Parkinson in animals which comprises administering to an animal in need of such treatment a therapeutically effective amount of a compound of claim 1.

3. A method of inhibiting prolactin secretion in animals which comprises administering to an animal in need of such treatment a therapeutically effective amount of a compound of claim 1.

4. A pharmaceutical composition useful in inhibiting prolactin secretion or treating Morbus Parkinson comprising a therapeutically effective amount of a compound of claim 1 in association with a pharmaceutical carrier or diluent.

5. A compound of claim 1, wherein $R_2$ is

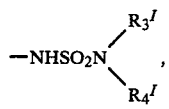

wherein $R_3{}^I$ and $R_4{}^I$ are alkyl or together $-[CH_2]_n-$, wherein n is from 3 to 5.

6. A compound of claim 1, wherein $R_5$ is $NR_6R_7$.

7. A compound of claim 6, wherein $R_6$ and $R_7$ are independently hydrogen or alkyl of 1 to 4 carbon atoms.

8. A compound of claim 6, wherein $R_6$ and $R_7$ are together a group $-[CH_2]_n-$, wherein n is a whole number from 3 to 7.

9. A compound of claim 6, wherein $R_6$ and $R_7$ are a group $-[CH_2]_2-A-[CH_2]_2-$, wherein A is oxygen, sulphur, or nitrogen substituted by alkyl of 1 to 4 carbon atoms or phenyl.

10. A compound of claim 9, wherein A is oxygen.
11. A compound of claim 9, wherein A is sulphur.
12. A compound of claim 9, wherein A is nitrogen substituted by alkyl of 1 to 4 carbon atoms, or phenyl.
13. A compound of claim 1, wherein X is hydrogen.
14. A compound of claim 1, wherein X is chlorine.
15. A compound of claim 1, wherein X is bromine.
16. A compound of claim 1, wherein $R_1$ is methyl.
17. A compound of claim 1, wherein $R_1$ is ethyl.
18. The compound of claim 1, which is 6-methyl-8α-N,N-dimethyl-sulphamylamino ergoline I.
19. A compound of claim 1, wherein X is H, $R_1$ is $CH_3$ and $R_3$ is H.
20. The compound of claim 1 in which $R_1$, $R_2$ and X are $CH_3$, $NR_3R_4$ and H, respectively, where $R_3$ and $R_4$ are H and $SO_2NH_2$, respectively.
21. The compound of claim 1 in which $R_1$, $R_2$ and X are $CH_3$, $NR_3R_4$ and H, respectively, where $R_3$ and $R_4$ are H and

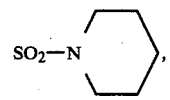

respectively.
22. The compound of claim 1 in which $R_1$, $R_2$ and X are $CH_3$, $NR_3R_4$ and H, respectively, where $R_3$ and $R_4$ are H and

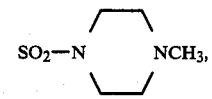

respectively.
23. The compound of claim 1 in which $R_1$ is methyl, X is hydrogen and $R_2$ is

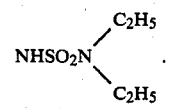

24. The compound of claim 1 in which $R_1$ is methyl, X is hydrogen and $R_2$ is $NHSO_2NH-C(CH_3)_3$.
25. The compound of claim 1 in which $R_1$ is methyl, X is hydrogen and $R_2$ is

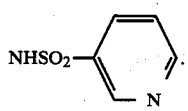

26. The compound of claim 1 in which $R_1$ is methyl, X is hydrogen and $R_2$ is

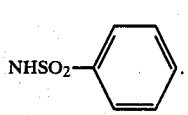

27. The compound of claim 1 in which $R_1$ is methyl, X is hydrogen and $R_2$ is $NH SO_2 CF_3$.

28. The compound of claim 1 in which $R_1$ is methyl, X is hydrogen and $R_2$ is $NH SO_2 CH_3$.
29. The compound of claim 1 in which $R_1$ is methyl, X is bromine and $R_2$ is
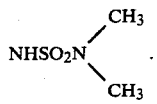
* * * * *